(12) United States Patent
Zhang et al.

(10) Patent No.: US 11,881,585 B2
(45) Date of Patent: Jan. 23, 2024

(54) BINDER COMPOUND, CONDUCTIVE BINDER, AND SECONDARY BATTERY CONTAINING SAME

(71) Applicant: Contemporary Amperex Technology Co., Limited, Ningde (CN)

(72) Inventors: Mengqin Zhang, Ningde (CN); Yanjie Zhao, Ningde (CN); Jianghui Lin, Ningde (CN); Xing Li, Ningde (CN); Haizu Jin, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

(21) Appl. No.: 18/048,445

(22) Filed: Oct. 21, 2022

(65) Prior Publication Data
US 2023/0107946 A1    Apr. 6, 2023

Related U.S. Application Data

(63) Continuation of application No. PCT/CN2021/120319, filed on Sep. 24, 2021.

(51) Int. Cl.
| | | |
|---|---|---|
| H01M 4/62 | (2006.01) | |
| C07C 329/06 | (2006.01) | |
| H01M 4/02 | (2006.01) | |

(52) U.S. Cl.
CPC ........... *H01M 4/623* (2013.01); *C07C 329/06* (2013.01); *H01M 4/625* (2013.01); *H01M 2004/021* (2013.01); *H01M 2004/028* (2013.01); *H01M 2220/20* (2013.01)

(58) Field of Classification Search
CPC .................................................. C07C 329/06
See application file for complete search history.

(56) References Cited

FOREIGN PATENT DOCUMENTS

| | | | |
|---|---|---|---|
| CN | 104262217 A | * | 1/2015 |
| CN | 105308081 A | * | 2/2016 |
| CN | 107298741 A | * | 10/2017 |
| CN | 107406529 A | | 11/2017 |
| CN | 107501484 A | | 12/2017 |
| JP | 2015-193842 | * | 11/2015 |
| JP | 2018515635 A | | 6/2018 |
| JP | 2022515059 A | | 2/2022 |
| KR | 20170129214 A | | 11/2017 |
| KR | 20210107019 A | | 8/2021 |
| WO | WO96/14289 | * | 5/1996 |
| WO | 2016149238 A1 | | 9/2016 |
| WO | 2020126448 A1 | | 6/2020 |

OTHER PUBLICATIONS 4-cyano-4-(((propylthio)carbonothioyl)thio)pentanoic acid, PubChem, available online at https://pubchem.ncbi.nlm.nih.gov/compound/89287551, date unknown.*
Machine translation of CN 107501484, published on Dec. 22, 2017 (Year: 2017).*
International Search Report received in PCT Application PCT/CN2021/120319 dated Jun. 21, 2020.
Written Opinion received in PCT Application PCT/CN2021/120319 dated Jun. 21, 2020.
English translation of International Search Report received in the corresponding international application PCT/CN2021/120319, dated Jun. 21, 2020.
Decision to Grant a Patent received in the corresponding Korean application 10-2022-7029614, dated Jun. 28, 2023.
First office action received in the corresponding Korean application 10-2022-7029614, dated Mar. 27, 2023.
The extended European search report received in the corresponding European application 21928351.2, dated Apr. 13, 2023.
Rezvani SJ et al: "Binder-induced surface structure evolution effects on Li-ion battery performance", Applied Surface Science, Elsevier, Amsterdam, NL, vol. 435, Nov. 21, 2017 (Nov. 21, 2017), pp. 1029-1036.
Guerre Marc et al: "One-pot synthesis of poly(vinylidene fluoride) methacrylate macromonomers via thia-Michael addition", Polymer Chemistry, vol. 7, No. 2, Jan. 1, 2016 (Jan. 1, 2016) , pp. 441-450.
Notice of Reasons of Refusal received in the corresponding Japanese application 2022-555732, dated Oct. 10, 2023.

* cited by examiner

*Primary Examiner* — Anca Eoff
(74) *Attorney, Agent, or Firm* — Kilpatrick Townsend & Stockton LLP

(57) ABSTRACT

A binder compound, a conductive binder, and a secondary battery containing the same are provided. In some embodiments, the binder compound of the present disclosure has a structure of formula (I), where $R^1$ and $R^2$ each independently represent a straight or branched $C_{1-12}$ alkyl; $R^3$ represents a halogen or cyano group; $R^4$ represents a hydroxymethyl or amino; Z represents a straight or branched $C_{1-12}$ alkylene; and m represents an integer selected from 7600-47000. The binder compound and the conductive binder of the present disclosure can improve the storage and cycle performances of the secondary battery.

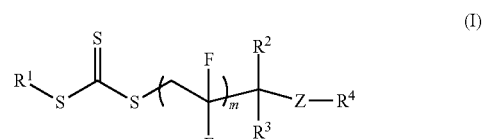

(I)

20 Claims, 3 Drawing Sheets

BINDER COMPOUND, CONDUCTIVE BINDER, AND SECONDARY BATTERY CONTAINING SAME

CROSS-REFERENCE TO RELATED APPLICATIONS

This application is a continuation of International Application PCT/CN2021/120319, filed on Sep. 24, 2021, and entitled "BINDER COMPOUND, CONDUCTIVE BINDER, AND SECONDARY BATTERY CONTAINING SAME", which is incorporated herein by reference in its entirety.

TECHNICAL FIELD

The present disclosure relates to the technical field of secondary batteries, in particular, to a binder compound, a conductive binder, and preparation methods thereof, and further relates to a secondary battery containing the conductive binder, a battery module, a battery pack, and a power consumption device.

BACKGROUND ART

In recent years, with the wide application of secondary batteries, people also have higher and higher requirements on the performances of the secondary batteries.

The internal resistance, storage, and cycle performance of the secondary batteries are affected in many ways, including dispersion of a conductive agent in an electrode plate material. However, as the conductive agent (such as carbon black) tends to agglomerate in a preparation process of the electrode plate of the battery, it is difficult to realized uniform distribution.

At present, the problem of agglomeration of the conductive agent (such as carbon black) in the industry is mainly alleviated by incorporating a dispersing agent, but the incorporation of the dispersing agent in turn may bring some adverse impacts on the battery.

Therefore, there is a need in the art for a technical solution that solves the problem of agglomeration of the conductive agent and improves the performances of the battery.

SUMMARY

Example Technical Problems Solved by the Present Disclosure

The present disclosure is carried out in view of the above subjects, aiming at addressing the agglomeration of the conductive agent in the stirring process, and further avoiding consequent deterioration of battery performances.

Technical Solutions for Solving the Problems

In order to achieve the objectives, in a first aspect, the present disclosure provides a binder compound, which has a structure of formula (I):

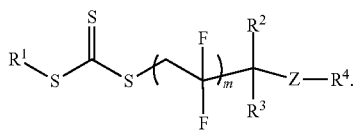

In the above, $R^1$ and $R^2$ each independently represent a straight or branched $C_{1-12}$ alkyl; $R^3$ represents a halogen or cyano group; $R^4$ represents a hydroxymethyl or amino; Z represents a straight or branched $C_{1-12}$ alkylene; and m represents an integer selected from 7600-47000, optionally from 7600-23100, more optionally from 19000-21000, and still more optionally from 19600-20500. The binder compound of the present disclosure can be used to for performing surface grafting modification for carbon-based conductive agent particles, thereby addressing the problem that the carbon-based conductive agent tends to agglomerate when the slurry is stirred, and further improving at least one of the performances such as storage and cycle without compromising the comprehensive performances of the secondary battery.

In some embodiments, $R^1$ and $R^2$ each independently represent a straight or branched $C_{2-8}$ alkyl, optionally a straight or branched $C_{2-6}$ alkyl; and/or, $R^3$ represents a cyano group; and/or, Z represents a straight or branched $C_{2-8}$ alkylene, and optionally a straight or branched $C_{2-6}$ alkylene.

In some embodiments, the binder compound of the present disclosure has the following structure:

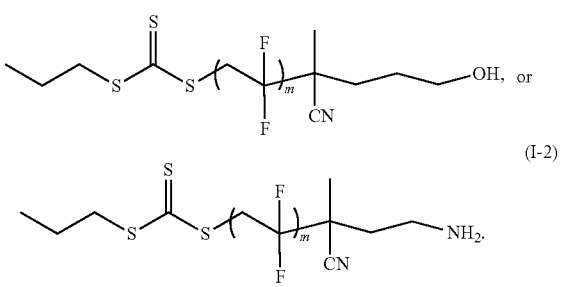

By selecting the structure of the binder compound, the binding capability thereof to a current collector and an electrode plate material and the chemical modification capability thereof to the carbon-based conductive agent can be further improved, and the capability thereof of addressing the agglomeration of the conductive agent can be further improved.

In a second aspect, the present disclosure further provides a preparation method of a binder compound, which includes the following steps:

(i) making, in the presence of an initiator, a chain transfer agent of formula (II) have polymerization reaction with a vinylidene fluoride monomer in a solvent:

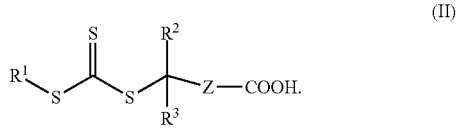

In the above, $R^1$ and $R^2$ each independently represent a straight or branched $C_{1-12}$ alkyl, $R^3$ represents a halogen or cyano group, and Z represents a straight or branched $C_{1-12}$ alkylene;

(ii) making a reaction product obtained in step (i) react with a reducing agent in a solvent to obtain a compound of the following formula (I); or (iii) making the reaction product obtained in step (i) react with an amination agent in a solvent; and (iv) making a reaction product obtained in step (iii) react with an oxidant under an alkaline condition, to obtain a binder compound of the following formula (I),

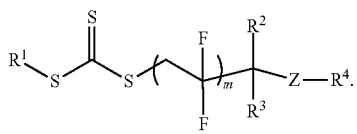
(I)

In the above, $R^1$-$R^3$ and Z are as defined in the above; $R^4$ represents a hydroxymethyl or amino; and m represents an integer selected from 7600-47000, optionally from 7600-23100, more optionally from 18000-21000, and still more optionally from 19600-20500.

Thus, the present disclosure provides a method of preparing the binder compound in the first aspect of the present disclosure.

In some embodiments, step (i) is carried out at 60-80° C., optionally at 65-75° C., and more optionally at 70° C. By selecting the temperature, the above steps are carried out at a desired reaction rate, to avoid a too low molecular weight of polymer or occurrence of implosion.

In some embodiments, a mass ratio of the chain transfer agent to the vinylidene fluoride monomer in step (i) is 1:1783-11029; optionally 1:1783-5421; more optionally 1:4400-5000; and still more preferably 1:4600-4800. By selecting the mass ratio of the chain transfer agent to the vinylidene fluoride monomer, control over the degree of polymerization (or molecular weight) of the resulting binder compound can be achieved.

In some embodiments, the chain transfer agent in step (i) is 4-cyano-4-(((propylthio)carbonothioyl)thio)pentanoic acid of formula (II-1):

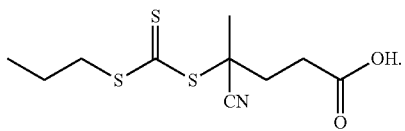
(II-1)

By selecting the chain transfer agent, the vinylidene fluoride monomer can be polymerized in a desirable manner to obtain the binder compound, and the binder compound thus obtained can effectively carry out the grafting modification for the conductive agent.

In some embodiments, step (ii) is carried out at −10-10° C., optionally at −5-5° C., more optionally at −5-0° C., and still more optionally at 0° C.

In some embodiments, step (iii) is carried out at 35-60° C., optionally at 40-45° C., and more optionally at 45° C.

In some embodiments, step (iv) is carried out at 15-50° C., optionally at 20-45° C., more optionally at 25-35° C., and still more optionally at 25° C.

By controlling various above steps within the above temperature ranges, it is conducive to control the reaction, and prevent the generation of by-products.

In a third aspect, the present disclosure provides a conductive binder, which contains a carbon-based conductive agent moiety and a binder moiety covalently linked to the carbon-based conductive agent moiety, wherein the binder moiety has a structure of formula (III):

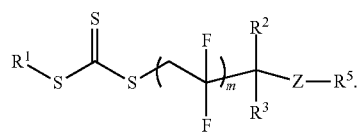
(III)

In the above, $R^1$ and $R^2$ each independently represent a straight or branched $C_{1-12}$ alkyl, $R^3$ represents a halogen or cyano group, $R^4$ represents a hydroxymethyl or amino; Z represents a straight or branched $C_{1-12}$ alkylene; and m represents an integer selected from 7600-47000, optionally from 7600-23100, more optionally from 19000-21000, and still more optionally from 19600-20500, $R^5$ represents #-$CH_2OC(O)$-* or #-$NHC(O)$-*, and # represents a position linked to Z, * indicates a position covalently linked to the carbon-based conductive agent moiety. The conductive binder of the present disclosure has both binding property and electric conductivity, and improves the dispersibility of conventional carbon-based conductive agents, and avoids the agglomeration.

In some embodiments, the binder moiety has the following structure:

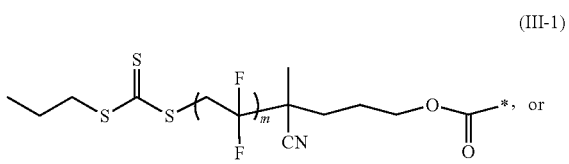
(III-1)

, or

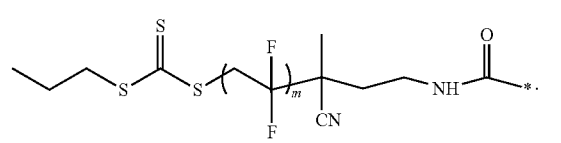
(III-2)

In the above, * indicates a position covalently linked to the carbon-based conductive agent moiety. The conductive binder having the binder moiety of the above structure can better achieve the effect of improving the agglomeration of the conductive agent.

In some embodiments, the mass ratio of the binder moiety to the carbon-based conductive agent moiety is 0.1-5:1, optionally 0.3-1:1. By selecting the mass ratio of the binder moiety to the carbon-based conductive agent moiety, it can be achieved that the obtained conductive binder can achieve good balance in binding performance, conductive performance, and agglomeration improvement.

In some embodiments, a specific surface area of the carbon-based conductive agent moiety is 1-3000 m²/g, optionally 10-1200 m²/g, and more optionally 20-800 m²/g. When the specific surface area of the carbon-based conductive agent moiety is in the ranges, a good balance between the binding property and the electric conductivity can be achieved, being conducive to improve the battery performances.

In some embodiments, the carbon-based conductive agent moiety is one or more selected from the group consisting of superconducting carbon, carbon black SP, acetylene black, ketjen black, carbon dots, carbon nanotube, graphene, and carbon nanofiber; optionally carbon black SP. By further selecting the carbon-based conductive agent moiety, the performances of the battery can be further improved.

In a fourth aspect, the present disclosure provides a preparation method of a conductive binder, which includes the following steps:

making a binder compound of formula (I), a carbon-based conductive agent, and a catalyst react in a solvent, to obtain a conductive binder:

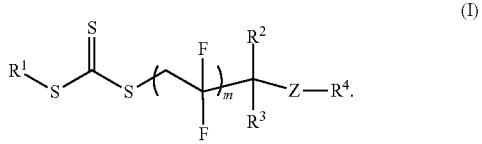

(I)

In the above, $R^1$ and $R^2$ each independently represent a straight or branched $C_{1-12}$ alkyl, $R^3$ represents a halogen or cyano group, $R^4$ represents a hydroxymethyl or amino; Z represents a straight or branched $C_{1-12}$ alkylene; and m represents an integer selected from 7600-47000, optionally from 7600-23100, more optionally from 19000-21000, and still more optionally from 19600-20500.

In some embodiments, $R^1$ and $R^2$ each independently represent a straight or branched $C_{2-8}$ alkyl, optionally a straight or branched $C_{2-6}$ alkyl; and/or, $R^3$ represents a cyano group; and/or, Z represents a straight or branched $C_{2-8}$ alkylene, and optionally a straight or branched $C_{2-6}$ alkylene.

In some embodiments, the binder compound of the formula (I) has the following structure:

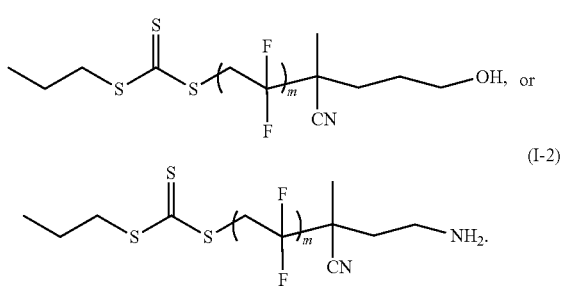

(I-1)

(I-2)

In some embodiments, the reaction is carried out at −5-5° C., optionally at 0° C., and more optionally at 0° C. By controlling the reaction temperature within the above ranges, it is easy to control the reaction rate.

In some embodiments, the mass ratio of the binder compound to the carbon-based conductive agent is 0.1-5:1, optionally 0.3-1:1. By controlling the mass ratio of the binder compound to the carbon-based conductive agent in the reaction, the obtained conductive binder can achieve good balance in binding property, electric conductivity, and agglomeration improvement, etc., further improving the battery performances.

In some embodiments, the carbon-based conductive agent is one or more selected from the group consisting of superconducting carbon, carbon black SP, acetylene black, ketjen black, carbon dots, carbon nanotube, graphene, and carbon nanofiber; optionally carbon black SP. By further selecting an appropriate carbon-based conductive agent, the performances of the battery can be further improved.

In some embodiments, a specific surface area of the carbon-based conductive agent is 1-3000 $m^2/g$, optionally 10-1200 $m^2/g$, and more optionally 20-800 $m^2/g$. By selecting the specific surface area of the carbon-based conductive agent in the above ranges, the obtained conductive binder can realize a balance between the electric conductivity and the agglomeration improvement, being favorable for improving the battery performances.

In a fifth aspect, the present disclosure provides use of the conductive binder in the third aspect of the present disclosure or the conductive binder prepared by the preparation method in the fourth aspect of the present disclosure in a secondary battery.

In a sixth aspect, the present disclosure provides a positive electrode plate, which includes a positive electrode current collector and a positive electrode material layer provided on at least one surface of the positive electrode current collector, wherein the positive electrode material layer contains the conductive binder in the third aspect of the present disclosure or the conductive binder prepared by the preparation method in the fourth aspect of the present disclosure. The conductive agent in the positive electrode material layer of the positive electrode plate of the present disclosure can be uniformly distributed without agglomeration, so as to improve the performances of the battery.

In some embodiments, the positive electrode material layer includes, based on a total weight of the positive electrode material layer, the conductive binder of 1-10 weight %, optionally 3-6 weight %. By controlling the content of the conductive binder in the positive electrode material layer within the above ranges, at least one of the cycle and storage performances of the battery can be improved.

In a seventh aspect, the present disclosure provides a secondary battery, including the positive electrode plate in the sixth aspect of the present disclosure.

In an eighth aspect, the present disclosure provides a battery module, including the secondary battery in the seventh aspect of the present disclosure.

In a ninth aspect, the present disclosure provides a battery pack, including the battery module in the eighth aspect of the present disclosure.

In a tenth aspect, the present disclosure provides a power consumption device, including at least one of the secondary battery in the seventh aspect of the present disclosure, the battery module in the eighth aspect of the present disclosure, or the battery pack in the ninth aspect of the present disclosure.

Compared with the prior art, the present disclosure at least has the following beneficial effects: the binder compound of the present disclosure capable of chemically bonding with the carbon-based conductive agent to be grafted on the surface thereof, so as prevent the conductive agent to agglomerate in the preparation of the electrode plate, thereby improving at least one of the storage performance and the cycle performance without compromising the comprehensive performances of the secondary battery.

ILLUSTRATION OF REFERENCE SIGNS

Figure 1:
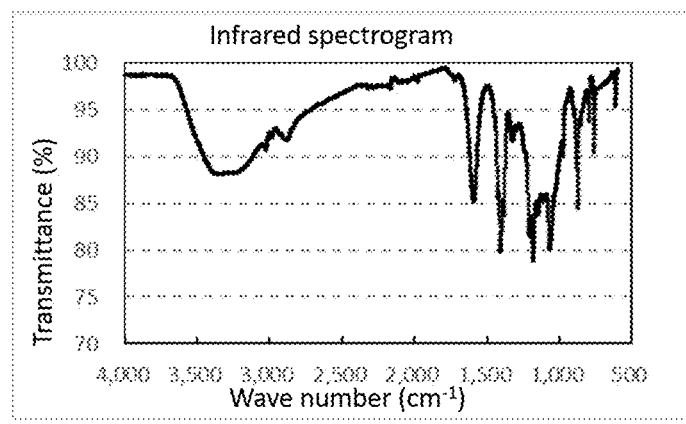
FIG. 1 is an infrared spectrogram of a conductive binder of Example 1.

1—battery pack; 2—upper case; 3—lower case; 4—battery module; 5—secondary battery; 51—housing; 52—electrode assembly; 53—cover plate.

DETAILED DESCRIPTION OF EMBODIMENTS

Before a binder compound, a conductive binder, a preparation method thereof, and use thereof of the present disclosure are described, it should be understood that the present disclosure is not limited to particular substances, methods, and experimental conditions described, as these may vary. It also should be understood that terms used herein are merely for the purpose of describing particular embodiments, and are not intended to be limiting, because the scope of the present disclosure will be limited only by the appended claims.

Unless otherwise defined, all of the technical and scientific terms used herein have the same meanings as those generally understood by those ordinarily skilled in the art. Any method and material similar or equivalent to those described herein can be used in the practice or test of the present disclosure, and it should be understood that modifications and variations are covered within the spirit and scope of the present disclosure.

For the sake of conciseness, the present disclosure specifically discloses some numerical ranges. However, any lower limit can be combined with any upper limit to form a range that is not explicitly disclosed; and any lower limit can be combined with other lower limits to form ranges that are not explicitly disclosed, and likewise, any upper limit can be combined with any other upper limit to form a range that is not explicitly disclosed. Besides, each separately disclosed point or individual numerical value can itself be combined, as a lower limit or an upper limit, with any other point or individual numerical value or with other lower limits or upper limits to form ranges that are not explicitly disclosed.

The "range" disclosed in the present disclosure is defined in the form of lower limit and upper limit, and a given range is defined by selecting a lower limit and an upper limit, wherein the selected lower limit and upper limit define boundaries of a particular range. A range defined in this manner can include end values or not, and can be arbitrarily combined, i.e., any lower limit can be combined with any upper limit to form a range. For example, if ranges of 60-120 and 80-110 are listed for a particular parameter, it is contemplated that ranges of 60-110 and 80-120 are also anticipated. Besides, if minimum range values listed are 1 and 2, and maximum range values listed are 3, 4, and 5, all of the following ranges can be anticipated: 1-3, 1-4, 1-5, 2-3, 2-4, and 2-5. In the present disclosure, unless otherwise stated, a numerical range "a-b" means an abbreviation of combination of any real numbers between a and b, where a and b are both real numbers. For example, a numerical range "0-5" means that all real numbers in "0-5" have been all listed herein, and "0-5" is just an abbreviation of combination of these numerical values. In addition, when a certain parameter is expressed as an integer greater than or equal to 2 ($\geq 2$), it is equivalent to disclosing that this parameter is, for example, an integer such as 2, 3, 4, 5, 6, 7, 8, 9, 10, 11, and 12.

If without special illustration, all the embodiments and optional embodiments of the present disclosure can be combined with each other to form new technical solutions.

If without special illustration, all the technical features and optional technical features of the present disclosure can be combined with each other to form new technical solutions.

If without special illustration, all steps of the present disclosure can be carried out in order, and also can be carried out randomly, preferably in order. For example, if the method includes steps (a) and (b), it means that the method can include steps (a) and (b) carried out in order, and also can include steps (b) and (a) performed in order. For example, reference to that the method further can include a step (c) means that the step (c) can be added to the method in any order, for example, the method can include steps (a), (b), and (c), also can include steps (a), (c), and (b), and also can include steps (c), (a), and (b), etc.

If without special illustration, terms "include (comprise)" and "contain" mentioned in the present disclosure are open-ended, and also can be close-ended. For example, the terms "include (comprise)" and "contain" can mean that other components that are not listed also can be included or contained, or only listed components can be included or contained.

If without special illustration, in the present disclosure, the term "or" is inclusive. For example, the phrase "A or B" means "A, B, or both A and B". More specifically, any of the following conditions satisfies the condition "A or B": A is true (or present) and B is false (or absent); A is false (or absent) and B is true (or present); or both A and B are true (or present).

In recent years, with the rapid development of new energy automobiles, people have higher and higher requirements on the performances of the secondary battery. Therefore, how to further improve the performances of the secondary battery has been a focus in the research and development of the secondary battery.

The internal resistance, storage performance, and cycle performance of the secondary battery are respectively affected by various factors, for example, material and thickness of a current collector, material of an electrode plate, compaction, moisture content, coating thickness, a separator, a conductive agent, an electrolytic solution, and a preparation process. Besides, the internal resistance and storage and cycle performances of the secondary battery are also affected by dispersion of the conductive agent in the electrode plate. Generally speaking, the more uniformly the conductive agent is distributed in the electrode plate material, the better the performances of the secondary battery will be. However, as the conductive agent (usually carbon black) tends to aggregate in the preparation process of the electrode plate, it is relatively hard to realize uniform distribution in the production practice.

At present, a main approach in the art is to incorporate a dispersing agent into an electrode plate material slurry, which alleviates the problem of agglomeration to a certain extent, but meanwhile, the addition of the dispersing agent also brings some adverse effects: on one hand, the dispersing agent has no positive contribution to the battery performances, and even on the contrary, reduces the proportion of the active material in the electrode plate material due to large amount of the dispersing agent remains therein, further reducing the energy density of the battery; and on the other hand, the addition of the dispersing agent also causes the preparation process of the electrode plate to be complicated and the costs to be increased.

In order to solve the above problems, the present disclosure provides a binder compound, which is capable of chemically reacting with a group (e.g., carboxyl) present on a surface of a particle of a carbon-based conductive agent (e.g., carbon black) to be grafted to a surface of the carbon-based conductive agent. Besides, the present disclosure further provides a conductive binder formed from a reaction of the binder compound of the present disclosure with a carbon-based conductive agent, which contains a carbon-based conductive agent moiety and a binder moiety, thus having both a binding function and a conductive function; moreover, the conductive binder is not easy to agglomerate when being mixed with other materials to prepare the electrode plate slurry, therefore, the conductive binder can be uniformly distributed in the electrode plate material layer to improve the battery performances.

Binder Compound

In a first aspect, the present disclosure provides a binder compound, which has a structure of formula (I):

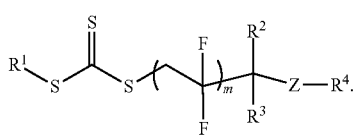

(I)

In the above, $R^1$ and $R^2$ each independently represent a straight or branched $C_{1-12}$ alkyl; $R^3$ represents a halogen or cyano group; $R^4$ represents a hydroxymethyl or amino; Z represents a straight or branched $C_{1-12}$ alkylene; and m represents an integer selected from 7600-47000, optionally from 7600-23100, more optionally from 19000-21000, and still more optionally from 19600-20500.

The binder compound of the present disclosure has a reactive group (e.g., a hydroxyl or an amino) at a terminal, and can form a conductive binder through surface grafting modification for carbon-based conductive agent particles by covalent bonding while having desirable binding performances, thus addressing the problem of agglomeration of the carbon-based conductive agent.

When the value of m is within the above ranges, the binder compound has strong binding capability, moderate reaction capacity and reaction rate with the carbon-based conductive agent, strong agglomeration resistance after being grafted with the carbon-based conductive agent, and relatively good solubility. During the preparation of a cathode slurry, the slurry has good stability, so that the electrode plate material is uniformly distributed, and the secondary battery prepared therefrom has good cycle and storage performances.

In some embodiments, in the above formula (I), $R^1$ and $R^2$ each independently represent a straight or branched $C_{2-8}$ alkyl, optionally a straight or branched $C_{2-6}$ alkyl; and/or, $R^3$ represents a cyano group; and/or, Z represents a straight or branched $C_{2-8}$ alkylene, and optionally a straight or branched $C_{2-6}$ alkylene.

In some embodiments, the binder compound of the present disclosure has the following structure:

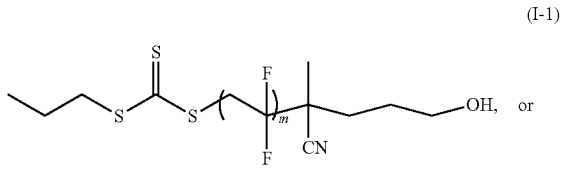

(I-1)

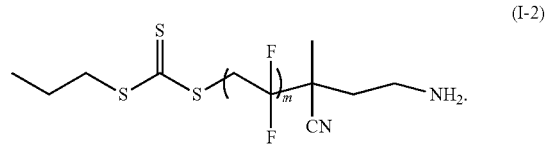

(I-2)

By selecting the structure of the binder compound, the binding capability of the binder compound to a current collector and an electrode plate material and the chemical modification capability thereof to the conductive agent can be further improved, and the capability thereof of addressing the agglomeration of the conductive agent can be further improved.

In some embodiments, a number average molecular weight (Mn) of the binder compounds of the present disclosure is 500000-3000000, optionally 500000-1500000. With the molecular weight being within the above appropriate ranges, the binder compound can possess suitable solubility and binding force, that is, the two can be well balanced by controlling the molecular weight within the above ranges.

In a second aspect, the present disclosure provides a preparation method of a binder compound, which includes the following steps:

making, in the presence of an initiator, a chain transfer agent of formula (II) have polymerization reaction with a vinylidene fluoride monomer in a solvent:

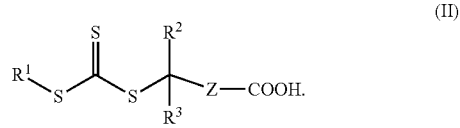

(II)

In the above, $R^1$ and $R^2$ each independently represent a straight or branched $C_{1-12}$ alkyl, $R^3$ represents a halogen or cyano group, and Z represents a straight or branched $C_{1-12}$ alkylene;

(1) making a reaction product obtained in step (i) react with a reducing agent in a solvent to obtain a compound of the following formula (I); or (2) making the reaction product obtained in step (i) react with an amination agent in a solvent; and (3) making a reaction product obtained in step (iii) react with an oxidant under an alkaline condition, to obtain a binder compound of the following formula (I),

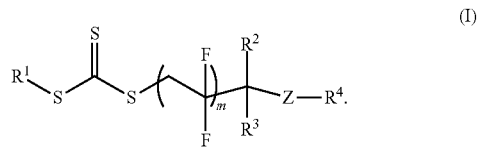

(I)

In the above, $R^1$-$R^3$ and Z are as defined in the above; $R^4$ represents a hydroxymethyl or amino; and m represents an integer selected from 7600-47000, optionally from 7600-23100, more optionally from 19000-21000, and still more optionally from 19600-20500.

The desirable binder compound can be prepared with the above method.

In some embodiments, in the above method, step (i) is carried out at 60-80° C., optionally at 65-75° C., and more optionally at 70° C. By controlling the temperature within the ranges, an appropriate reaction rate can be obtained, so as to avoid a too low molecular weight or occurrence of implosion.

In some embodiments, the reaction of step (i) is carried out under an oxygen-free condition. In some embodiments, optionally, the reaction of step (i) is carried out in an inert gas atmosphere. In some embodiments, optionally, the reaction of step (i) is carried out in a $N_2$ atmosphere. Thus, free radicals can be prevented from being oxidized, the reaction is allowed to proceed as desired, and the side effects are reduced.

In some embodiments, the initiator in step (i) is an initiator known in the art that can be used in the reaction. In some embodiments, the initiator is azobisisobutyronitrile (AIBN) or benzoyl peroxide (BPO). Optionally, in some embodiments, the initiator is azobisisobutyronitrile.

In some embodiments, the solvent in step (i) is tetrahydrofuran (THF), dimethylformamide (DMF), or dimethylsulfoxide (DMSO); and optionally, the solvent in step (i) is tetrahydrofuran.

In some embodiments, a mass ratio of the chain transfer agent to the vinylidene fluoride monomer in step (i) is 1:1783-11029; optionally 1:1783-5421; more optionally 1:4400-5000; and still more preferably 1:4600-4800. By selecting the mass ratio of the chain transfer agent to the vinylidene fluoride monomer used in the method, control over the degree of polymerization (or molecular weight) of the resulting binder compound can be achieved.

In some embodiments, the chain transfer agent in step (i) is 4-cyano (propylthiocarbonyl) thiopentanoic acid (CPP) of formula (II-1):

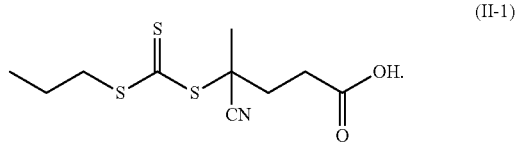 [SMILES: CCCSC(=S)SC(C)(C#N)CCC(=O)O]

(II-1)

The inventor(s) found that by using the chain transfer agent of formula (II), optionally the chain transfer agent of formula (II-1), the method of the present disclosure can make the vinylidene fluoride monomer have polymerization in a manner of high polymerization speed, high controllability of polymerization molecular weight, good molecular weight uniformity (i.e., small polymer dispersity index (PDI)) so as to obtain the binder compound of the present disclosure, and the binder compound thus obtained can effectively perform the grafting modification for the conductive agent.

In some embodiments, the solvent in step (ii) is tetrahydrofuran, dimethylformamide, or dimethylsulfoxide; and optionally, the solvent in step (ii) is tetrahydrofuran. In some embodiments, the reducing agent in step (ii) is $LiAlH_4$. In some embodiments, step (ii) is carried out at −10-10° C., optionally at −5-5° C., more optionally at −5-0° C., and still more optionally at 0° C.

In some embodiments, the solvent in step (iii) is methanol. In some embodiments, the amination agent in step (iii) is ammonia gas. In some embodiments, step (iii) is carried out at 35-60° C., optionally at 40-45° C., and more optionally at 45° C.

In some embodiments, the oxidant in step (iv) is sodium hypochlorite. In some embodiments, step (iv) is carried out in the presence of NaOH. In some embodiments, step (iv) is carried out at 15-50° C., optionally at 20-45° C., more optionally at 25-35° C., and still more optionally at 25° C. By using the above reaction conditions, it is easy to control the reaction, and generation of by-products is prevented.

In some embodiments, the method of the present disclosure further can optionally include a post-treatment step. As can be understood by those skilled in the art, the post-treatment step can include a conventional post-treatment method selected according to nature of a product, for example, filtering, washing, and drying.

Conductive Binder

In a third aspect, the present disclosure provides a conductive binder, which contains a carbon-based conductive agent moiety and a binder moiety covalently linked to the carbon-based conductive agent moiety, wherein the binder moiety has a structure of formula (III):

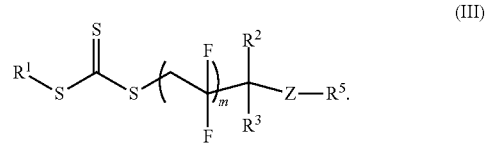

(III)

In the above, $R^1$ and $R^2$ each independently represent a straight or branched $C_{1-12}$ alkyl; $R^3$ represents a halogen or cyano group; $R^4$ represents a hydroxymethyl or amino; Z represents a straight or branched $C_{1-12}$ alkylene; m represents an integer selected from 7600-47000, optionally from 7600-23100, more optionally from 19000-21000, and still more optionally from 19600-20500; $R^5$ represents #-$CH_2OC$(O)-* or #-NHC(O)-*, and # represents a position linked to Z, * indicates a position covalently linked to the carbon-based conductive agent moiety.

The conductive binder of the present disclosure has both binding property and electric conductivity, and improves the dispersibility of conventional carbon-based conductive agents, and avoids the agglomeration. Therefore, in the preparation process of the positive electrode slurry, by replacing the binder and the conductive agent separately added in the prior art with the conductive binder of the present disclosure, the problem that the conductive agent tends to aggregate in the stirring process to cause deterioration of the battery performances can be solved from the source.

Besides, those skilled in the art could readily understand that the working efficiency can be improved by using the conductive binder of the present disclosure to replace the binder and the conductive agent added in separate feeding steps.

Herein, the terms "covalently link" or "covalently bind" or "linked by a covalent bond" and like expressions are used interchangeably, meaning that atoms, molecules, or various parts of the molecule are linked together by a covalent bond.

In some embodiments, in the conductive binder of the present disclosure, the binder moiety has the following structure:

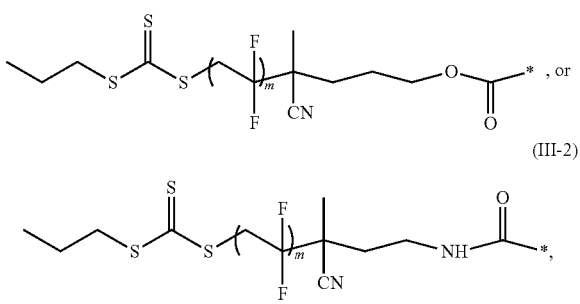

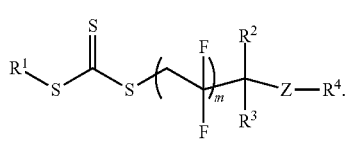

i. indicates a position covalently linked to the carbon-based conductive agent moiety.

In some embodiments, the mass ratio of the binder moiety to the carbon-based conductive agent moiety in the conductive binder is 0.1-5:1, optionally 0.3-1:1.

In the conductive binder of the present disclosure, the mass ratio of the binder moiety to the carbon-based conductive agent moiety affects the binding property and electric conductivity thereof, and further will affect the battery performances. When the mass ratio of the binder moiety to the carbon-based conductive agent moiety is in a range of 0.1-5:1, optionally 0.3-1:1, the conductive binder has good binding force and electric conductivity, thus obtaining good electric conductivity of the electrode plate; meanwhile, as the surface of the conductive agent particles has an appropriate grafting amount of the binder moiety, the agglomeration is significantly improved; further, the cycle performance and the storage performance of the secondary battery containing the electrode plate or the conductive binder of the present disclosure are improved.

In some embodiments, a specific surface area of the carbon-based conductive agent moiety is 1-3000 $m^2/g$, optionally 10-1200 $m^2/g$, and more optionally 20-800 $m^2/g$.

The specific surface area of the carbon-based conductive agent will directly affect the electric conductivity of the electrode plate. When the carbon-based conductive agent moiety in the conductive binder has the specific surface area within the above ranges, the conductive binder can desirably alleviate or avoid agglomeration, and can have good binder property and electric conductivity, so that material layers of the electrode plate are firmly bound and have good electric conductivity, being conducive to improve the battery performances.

The carbon-based conductive agent moiety of the present disclosure can be selected from various conventional carbon-based conductive agents in the art. In some embodiments, the carbon-based conductive agent moiety is one or more selected from, but not limited to, the group consisting of superconducting carbon, carbon black (such as carbon black SP, acetylene black, and ketjen black), carbon dots, carbon nanotube, graphene, and carbon nanofiber. In some embodiments, optionally, the carbon-based conductive agent is carbon black. As the carbon black, various commercially available carbon blacks, for example, furnace black, can be used. In some embodiments, more optionally, the carbon-based conductive agent moiety is carbon black SP. By further selecting the carbon-based conductive agent moiety, the performances of the battery can be further improved.

In a fourth aspect, the present disclosure provides a preparation method of a conductive binder, which includes the following steps:

making a binder compound of formula (I), a carbon-based conductive agent, and a catalyst react in a solvent, to obtain a conductive binder:

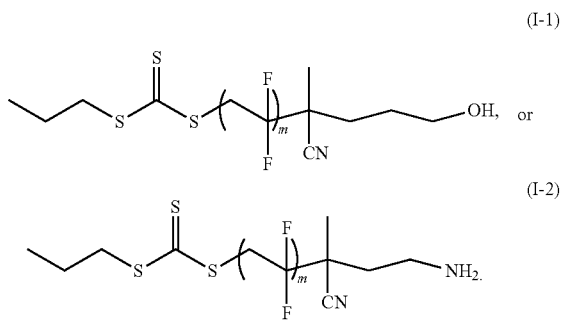

In the above, $R^1$ and $R^2$ each independently represent a straight or branched $C_{1-12}$ alkyl, $R^3$ represents a halogen or cyano group, $R^4$ represents a hydroxymethyl or amino; Z represents a straight or branched $C_{1-12}$ alkylene; and m represents an integer selected from 7600-47000, optionally from 7600-23100, more optionally from 19000-21000, and still more optionally from 19600-20500.

In some embodiments, in the formula (I), $R^1$ and $R^2$ each independently represent a straight or branched $C_{2-8}$ alkyl, optionally a straight or branched $C_{2-6}$ alkyl; and/or, $R^3$ represents a cyano group; and/or, Z represents a straight or branched $C_{2-8}$ alkylene, and optionally a straight or branched $C_{2-6}$ alkylene.

In some embodiments, the binder compound of the formula (I) has the following structure:

In some embodiments, in the above method, the solvent is tetrahydrofuran (THF), dimethylformamide (DMF), dimethylsulfoxide (DMSO) or pyridine; and optionally, the solvent is tetrahydrofuran or pyridine. More preferably, in the above method, if the binder compound of formula (I-1) is used, the solvent is tetrahydrofuran. More optionally, in the above method, if the binder compound of formula (I-2) is used, the solvent is pyridine.

In some embodiments, the above method uses a low temperature condition. In some embodiments, the reaction is carried out at a temperature of -5-5° C., optionally -5-0° C., and more optionally 0° C. With the reaction temperature being within the ranges, it is easy to control the reaction rate, and other side reactions are avoided.

In some embodiments, this step is carried out in the presence of a catalyst. When a terminal group of the binder compound is a hydroxyl group, the catalyst can be, for example, 1-(3-dimethylaminopropyl)-3-ethylcarbodiimide hydrochloride (EDC), and N-hydroxysuccinimide (NHS); and when the terminal group of the binder compound is an amino group, the catalyst can be, for example, sulfoxide chloride ($SOCl_2$).

When the terminal group of the binder compound is an amino group, in some embodiments, the steps of the method can be performed in an alkaline environment. The alkaline environment can be realized by adding an alkaline substance to the solvent, e.g. adding triethylamine.

In some embodiments, in the above method, the reaction is carried out under stirring.

In some embodiments, the mass ratio of the binder compound to the carbon-based conductive agent is 0.1-5:1, optionally 0.3-1:1. By controlling the mass ratio of the binder compound to the carbon-based conductive agent in the reaction, the obtained conductive binder can achieve balance in terms such as binding property, electric conductivity, and agglomeration improvement, further improving the battery performances.

In some embodiments, the carbon-based conductive agent is one or more selected from the group consisting of superconducting carbon, carbon black (such as carbon black SP, acetylene black, and ketjen black), carbon dots, carbon nanotube, graphene, and carbon nanofiber. In some embodiments, optionally, the carbon-based conductive agent is carbon black. In some embodiments, more optionally, the carbon-based conductive agent is carbon black SP. By selecting the appropriate carbon-based conductive agent, the performances of the battery can be further improved.

In some embodiments, a specific surface area of the carbon-based conductive agent is 1-3000 m$^2$/g, optionally 10-1200 m$^2$/g, and more optionally 20-800 m$^2$/g. By selecting the specific surface area of the carbon-based conductive agent to be within the above ranges, the obtained conductive binder can achieve balance between the electric conductivity and the agglomeration improvement, being conducive to improve the battery performances.

The conductive binder of the present disclosure can be used in the preparation of a positive electrode plate in a secondary battery.

Positive Electrode Plate

In a sixth aspect, the present disclosure provides a positive electrode plate, which includes a positive electrode current collector and a positive electrode material layer provided on at least one surface of the positive electrode current collector, wherein the positive electrode material layer contains the conductive binder in the third aspect of the present disclosure or the conductive binder prepared by the preparation method in the fourth aspect of the present disclosure. The conductive agent in the positive electrode material layer of the positive electrode plate of the present disclosure can be uniformly distributed without agglomeration, so as to improve the performances of the battery.

In some embodiments, the positive electrode material layer includes, based on a total weight of the positive electrode material layer, the conductive binder of 1-10 weight %, preferably 3-6 weight %. When the content of the conductive binder in the positive electrode material layer in the present disclosure is within the above ranges, the electrode plate has good electric conductivity and small impedance, the overall polarization of the battery core is relatively small, and the cycle and storage performances of the secondary battery are obviously improved. After the content of the conductive binder in the positive electrode material layer reaches 6 weight %, the cycle and storage performances of the battery are not greatly improved with the increase of the content. When the content of the conductive binder exceeds 10 weight %, the storage and cycle performances of the battery have no obvious trend of being continuously improved compared with that when the content does not exceed 10 weight %, but the battery capacity is reduced as the load of the positive electrode active material in the electrode plate is sacrificed at this point. Therefore, when the positive electrode material layer of the electrode plate contains the conductive binder of 1-10 weight %, optionally 3-6 weight %, the secondary battery obtained from such electrode plate has the best comprehensive performances, i.e., has both improved storage and cycle performances and good capacity.

As an example, the positive electrode current collector has two surfaces opposite to each other in its own thickness direction, and the positive electrode material layer is provided on either or both of the two opposite surfaces the positive electrode current collector.

In some embodiments, a metallic foil or a composite current collector may be used as the positive electrode current collector. For example, aluminum foil may be used as the metallic foil. The composite current collector may include a polymer material base layer and a metal layer formed on at least one surface of the polymer material base layer. The composite current collector can be formed by forming a metal material (aluminum, aluminum alloy, nickel, nickel alloy, titanium, titanium alloy, silver, and silver alloy, etc.) on a polymer material substrate (e.g., a substrate of polypropylene (PP), polyethylene terephthalate (PET), polybutylene terephthalate (PBT), polystyrene (PS), and polyethylene (PE)).

The positive electrode material layer further contains a positive electrode active material. In some embodiments, the positive electrode active material may use a positive electrode active material for the battery well known in the art. As an example, the positive electrode active material may include at least one of the following materials: olivine-structured lithium-containing phosphates, lithium transition metal oxides and their respective modified compounds. However, the present disclosure is not limited to these materials, and other conventional materials that can be used as a positive electrode active material of a battery also may be used. These positive electrode active materials may be used alone or a combination of two or more may be used. In the above, examples of the lithium transition metal oxide may include, but are not limited to, at least one of lithium cobalt oxide (e.g., $LiCoO_2$), lithium nickel oxide (e.g., $LiNiO_2$), lithium manganese oxide (e.g., $LiMnO_2$, $LiMn_2O_4$), lithium nickel cobalt oxide, lithium manganese cobalt oxide, lithium nickel manganese oxide, lithium nickel cobalt manganese oxide (e.g., $LiNi_{1/3}Co_{1/3}Mn_{1/3}O_2$ (also referred to as $NCM_{333}$ for short), $LiNi_{0.5}Co_{0.2}Mn_{0.3}O_2$ (also referred to as $NCM_{523}$ for short), $LiNi_{0.5}Co_{0.25}Mn_{0.25}O_2$ (also referred to as $NCM_{211}$ for short), $LiNi_{0.6}Co_{0.2}Mn_{0.2}C_2$ (also referred to as $NCM_{622}$ for short), $LiNi_{0.8}Co_{0.1}Mn_{0.1}O_2$ (also referred to as $NCM_{811}$ for short), lithium nickel cobalt aluminum oxide (e.g., $LiNi_{0.85}Co_{0.15}Al_{0.05}O_2$), and modified compounds thereof. Examples of the olivine-structured lithium-containing phosphate may include, but are not limited to, at least one of lithium iron phosphate (e.g., $LiFePO_4$ (also referred to as LFP for short)), a composite material of lithium iron phosphate and carbon, lithium manganese phosphate (e.g., $LiMnPO_4$), a composite material of lithium manganese phosphate and carbon, lithium iron manganese phosphate, and a composite material of lithium iron manganese phosphate and carbon.

In some embodiments, the positive electrode material layer further optionally includes other binders. As an example, the binder may include at least one of polyvinylidene fluoride (PVDF) binder, polytetrafluoroethylene (PTFE), vinylidene fluoride-tetrafluoroethylene-propylene terpolymer, vinylidene fluoride-hexafluoropropylene-tetrafluoroethylene terpolymer, tetrafluoroethylene-hexafluoropropylene copolymer, and fluorine-containing acrylate resin which are conventional in the field.

In some embodiments, the positive electrode plate may be prepared in a following manner: dispersing the foregoing components for preparing the positive electrode plate, for example, the positive electrode active material, the conductive agent, and any other components in a solvent (for example, N-methylpyrrolidone), to form a positive electrode slurry; and coating the positive electrode slurry on the positive electrode current collector, followed by procedures such as drying and cold pressing, to obtain the positive electrode plate.

Second Battery

In a seventh aspect, the present disclosure provides a secondary battery, which includes the positive electrode plate in the sixth aspect of the present disclosure. Generally, the secondary battery includes a positive electrode plate, a negative electrode plate, an electrolyte, and a separator. In a charging and discharging process of the battery, active ions are inserted (embedded) and extracted back and forth between the positive electrode plate and the negative electrode plate. The electrolyte plays a role of conducting ions between the positive electrode plate and the negative electrode plate. The separator is provided between the positive electrode plate and the negative electrode plate, and mainly plays a role of preventing short circuit of positive and negative electrodes, and meanwhile can make the ions pass through.

In some embodiments, the secondary battery is a lithium-ion secondary battery.

[Negative Electrode Plate]

The negative electrode plate includes a negative electrode current collector and a negative electrode material layer provided on at least one surface of the negative electrode current collector, and the negative electrode material layer includes a negative electrode active material.

As an example, the negative electrode current collector has two surfaces opposite to each other in its own thickness direction, and the negative electrode material layer is provided on either or both of the two opposite surfaces the negative electrode current collector.

In some embodiments, a metallic foil or a composite current collector may be used as the negative electrode current collector. For example, copper foil may be used as the metallic foil. The composite current collector may include a polymer material base layer and a metal layer formed on at least one surface of the polymer material substrate. The composite current collector can be formed by forming a metal material (copper, copper alloy, nickel, nickel alloy, titanium, titanium alloy, silver, and silver alloy, etc.) on a polymer material substrate (e.g., a substrate of polypropylene (PP), polyethylene terephthalate (PET), polybutylene terephthalate (PBT), polystyrene (PS), and polyethylene (PE)).

In some embodiments, the negative electrode active material may use a negative electrode active material for the battery well known in the art. As an example, the negative electrode active material may include at least one of the following materials: artificial graphite, natural graphite, soft carbon, hard carbon, silicon-based material, tin-based material, and lithium titanate, etc. The silicon-based material may be at least one selected from the group consisting of elemental silicon, a silicon-oxygen compound, a silicon-carbon composite, a silicon-nitrogen composite, and a silicon alloy. The tin-based material may be at least one selected from the group consisting of elemental tin, a tin oxide compound, and a tin alloy. However, the present disclosure is not limited to these materials, and other conventional materials that can be used as a negative electrode active material of a battery also may be used. These negative electrode active materials may be used alone or a combination of two or more may be used.

In some embodiments, the negative electrode material layer further optionally includes a binder. The binder may be at least one selected from the group consisting of styrene-butadiene rubber (SBR), polyacrylic acid (PAA), polyacrylic acid sodium (PAAS), polyacrylamide (PAM), polyvinyl alcohol (PVA), sodium alginate (SA), polymethacrylic acid (PMAA), and carboxymethyl chitosan (CMCS).

In some embodiments, the negative electrode material layer further optionally includes a conductive agent. The conductive agent may be at least one selected from the group consisting of superconducting carbon, acetylene black, carbon black, ketjen black, carbon dots, carbon nanotube, graphene, and carbon nanofiber.

In some embodiments, the negative electrode material layer further optionally includes other auxiliary agents, for example, a thickening agent (such as sodium carboxymethyl cellulose (CMC-Na)).

In some embodiments, the negative electrode plate may be prepared in a following manner: dispersing the foregoing components for preparing the negative electrode plate, for example, the negative electrode active material, the conductive agent, the binder, and any other components in a solvent (for example, deionized water), to form a negative electrode slurry; and coating the negative electrode slurry on the negative electrode current collector, followed by procedures such as drying and cold pressing, to obtain the negative electrode plate.

[Electrolyte]

The electrolyte plays a role of conducting ions between the positive electrode plate and the negative electrode plate. The type of the electrolyte is not specifically limited in the present disclosure, and may be selected as required. For example, the electrolyte may be liquid, gel, or all-solid.

In some embodiments, the electrolyte is an electrolytic solution. The electrolytic solution includes an electrolyte salt and a solvent.

An electrolyte salt for a secondary battery well known in the art may be used as the electrolyte salt. In some embodiments, the electrolyte salt may be at least one selected from the group consisting of lithium hexafluorophosphate, lithium tetrafluoroborate, lithium perchlorate, lithium hexafluoroarsenate, lithium bisfluorosulfonimide, lithium bistrifluoromethanesulfonimide, lithium trifluoromethanesulfonate, lithium difluorophosphate, lithium difluorooxalato borate, lithium bisoxalate borate, lithium difluorobisoxalate phosphate, and lithium tetrafluorooxalate phosphate.

In some embodiments, the solvent may be at least one selected from the group consisting of ethylene carbonate, propylene carbonate, ethyl methyl carbonate, diethyl carbonate, dimethyl carbonate, dipropyl carbonate, methyl propyl carbonate, ethyl propyl carbonate, butylene carbonate, fluoroethylene carbonate, methyl formate, methyl acetate, ethyl acetate, propyl acetate, methyl propionate, ethyl propionate, propyl propionate, methyl butyrate, ethyl butyrate, 1,4-butyrolactone, sulfolane, dimethylsulfone, methylsulfone acetate, and diethyl sulfone.

In some embodiments, the electrolytic solution further optionally includes an additive. For example, the additive may include a negative electrode film-forming additive and a positive electrode film-forming additive, and further may include an additive capable of improving certain performances of the battery, for example, an additive improving overcharge performance of the battery and an additive improving high temperature or low temperature performance of the battery.

[Separator]

In some embodiments, the secondary battery further includes a separator. The type of the separator is not particularly limited in the present disclosure, and any well-known porous-structured separator having good chemical stability and mechanical stability can be selected.

In some embodiments, the material of the separator may be at least one selected from the group consisting of glass fiber, non-woven fabric, polyethylene, polypropylene, and polyvinylidene fluoride. The separator may be a single-layer thin film, and also may be a multi-layer composite thin film, which is not particularly limited. When the separator is a multi-layer composite thin film, materials of various layers may be the same or different, and are not particularly limited.

In some embodiments, the positive electrode plate, the negative electrode plate, and the separator may be fabricated into an electrode assembly through a winding process or a lamination process.

In some embodiments, the secondary battery may include an outer package. The outer package can be used to encapsulate the above electrode assembly and electrolyte.

In some embodiments, the outer package of the secondary battery may be a hard shell, for example, a hard plastic shell, an aluminum shell, and a steel shell. The outer package of the secondary battery also may be a soft package, for example, a pouch type soft package. The material of the soft package may be plastic, and examples of the plastic may include polypropylene, polybutylene terephthalate, and polybutylene succinate, etc.

Figure 3:
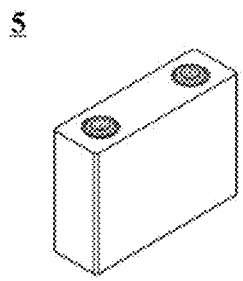
FIG. 3 is a schematic view of a secondary battery in an embodiment of the present disclosure.

There is no particular limitation on the shape of the secondary battery in the present disclosure, and it may be cylindrical, square or in any other arbitrary shapes. For example, FIG. 3 shows a secondary battery 5 of a square structure as an example.

Figure 4:
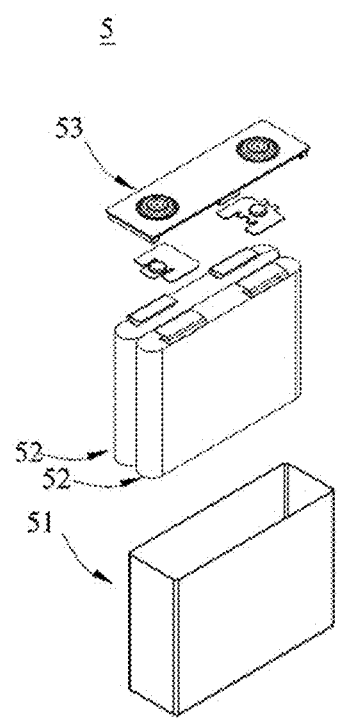
FIG. 4 is an exploded view of the secondary battery in an embodiment of the present disclosure shown in FIG. 3.

In some embodiments, referring to FIG. 4, the outer package may include a housing 51 and a cover plate 53. In the above, the housing 51 may include a bottom plate and a side plate connected to the bottom plate, and the bottom plate and the side plate are enclosed to form an accommodating cavity. The housing 51 has an opening in communication with the accommodating cavity, and the cover plate 53 can be provided to cover the opening so as to close the accommodating cavity. The positive electrode plate, the negative electrode plate, and the separator can form an electrode assembly 52 through a winding process or a lamination process. The electrode assembly 52 is encapsulated in the accommodating cavity. The electrolytic solution is soaked in the electrode assembly 52. The number of electrode assemblies 52 contained in the secondary battery 5 can be one or more, and those skilled in the art could make a selection according to actual requirements.

In some embodiments, the secondary batteries can be assembled into a battery module, the number of secondary batteries contained in the battery module may be one or more, and those skilled in the art could select the specific number according to the application and capacity of the battery module.

Figure 5:
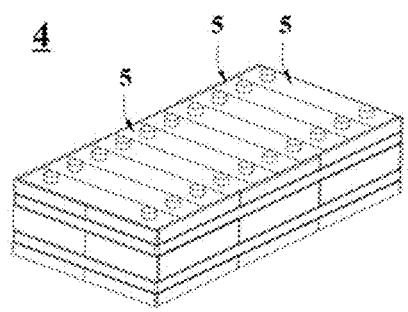
FIG. 5 is a schematic view of a battery module in an embodiment of the present disclosure.

FIG. 5 shows a battery module 4 as an example. Referring to FIG. 5, in the battery module 4, a plurality of secondary batteries 5 may be sequentially arranged in a length direction of the battery module 4. Without doubt, the secondary batteries also may be arranged in any other manners. Further, the plurality of secondary batteries 5 may be fixed by fasteners.

Optionally, the battery module 4 further may include an enclosure having an accommodating space, and the plurality of secondary batteries 5 are accommodated in the accommodating space.

In some embodiments, the above battery module further may be assembled into a battery pack, the number of battery modules contained in the battery pack may be one or more, and the specific number could be selected by those skilled in the art according to the application and capacity of the battery pack.

Figure 6:
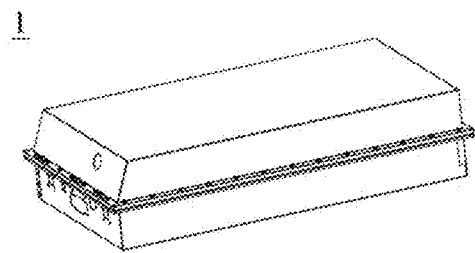
FIG. 6 is a schematic view of a battery pack in an embodiment of the present disclosure.
Figure 7:
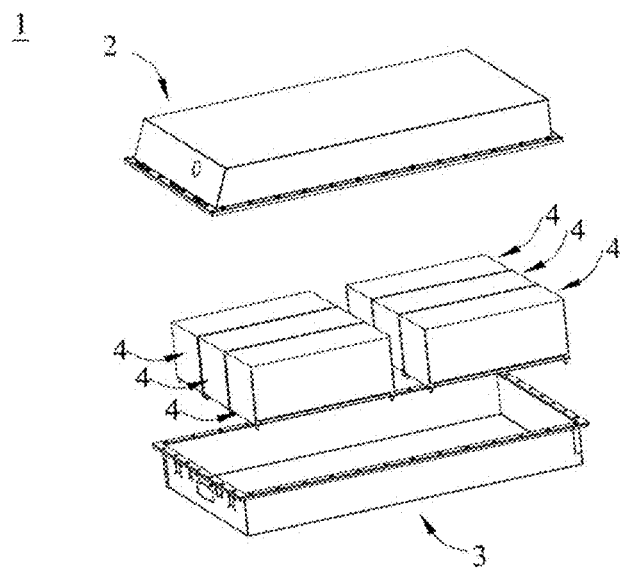
FIG. 7 is an exploded view of the battery pack in an embodiment of the present disclosure shown in FIG. 6.

FIG. 6 and FIG. 7 show a battery pack 1 as an example. Referring to FIG. 6 and FIG. 7, a battery box and a plurality of battery modules 4 provided in the battery box may be included in the battery pack 1. The battery box includes an upper box body 2 and a lower box body 3, and the upper box body 2 can be provided to cover the lower box body 3, to form a closed space for accommodating the battery modules 4. The plurality of battery modules 4 may be arranged in the battery box in an arbitrary manner.

In addition, the present disclosure further provides a power consumption device, wherein the power consumption device includes the secondary battery, the battery module, or the battery pack provided in the present disclosure. The secondary battery, the battery module, or the battery pack can be used as a power supply of the power consumption device, and also can be used as an energy storage unit of the power consumption device. The power consumption device may include a mobile device (for example, a mobile phone, a notebook computer), an electric vehicle (for example, a battery electric vehicle, a hybrid electric vehicle, a plug-in hybrid electric vehicle, an electric bicycle, an electric scooter, an electric golf cart, an electric truck), an electric train, a ship and a satellite, an energy storage system, etc., but is not limited thereto.

For the power consumption device, the secondary battery, the battery module or the battery pack may be selected in accordance with use requirements thereof.

Figure 8:
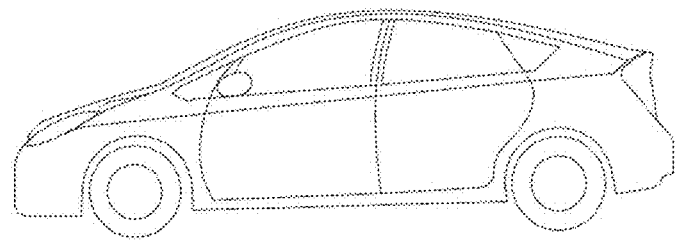
FIG. 8 is a schematic view of a power consumption device using the secondary battery in an embodiment of the present disclosure as a power supply.

FIG. 8 shows a power consumption device as an example. This power consumption device is a battery electric vehicle, a hybrid electric vehicle, a plug-in hybrid electric vehicle, etc. In order to meet the requirements of the power consumption device for high power and high energy density of the secondary battery, the battery pack or the battery module can be used.

The device as another example may be a mobile phone, a tablet computer, a notebook computer, etc. The device is generally required to be light and thin, and may use the secondary battery as a power supply.

EXAMPLE

Hereinafter, examples of the present disclosure are described. The examples described below are exemplary, and merely used to explain the present disclosure, but cannot be construed as limitation to the present disclosure.

Where specific techniques or conditions are not specified in the examples, they are carried out according to techniques or conditions described in documents in the art or according to product specifications.

If manufacturers of reagents or apparatuses used are not specified, all of them are conventional products commercially available.

Test Method

Infrared Spectrum Test

The structural composition of the conductive binder of the examples was measured with a Model IS10 Fourier Transform infrared spectrometer from Nicolet Company, US, according to the standard GB/T6040-2002 infrared spectrogram analytical method. The test wave number ranged 600~4000 cm$^{-1}$.

Number Average Molecular Weight (Mn) Test

The number average molecular weight (Mn) of the binder compound obtained in various examples was measured by using Japanese Tosoh Corporation HLC-8320GPC gel permeation chromatography (GPC), SuperMultipore HZ series semi-micro SEC column, and standard PS polystyrene.

Test method was dissolving 2 mg of a to-be-tested substance in 2 mL of a GPC-specific dimethylformamide (DMF) solvent, sampling 2.5 μL, and performing the test according to the following parameters:

pump capacity: 0.05 mL/min;
filling volume: 200 μL;
temperature control range: 45° C.; and
data acquisition frequency: 100 Hz.

Battery Capacity Test

The battery capacity was tested with a Hopetech CHT3568 battery capacity tester at 25° C. with a current of 0.33 C and a voltage of 2.8-4.35 V.

Test of a Binding Force of the Electrode Plate

An electrode plate was taken, and cut to obtain a test sample having a length of 100 mm and a width of 10 mm. A stainless steel plate with a width of 25 mm was taken, and pasted with a double-sided adhesive (with a width of 11 mm), one side of the test sample coated with the positive electrode material was pasted onto the double-sided adhesive on the stainless steel plate, and a surface thereof was rolled and compressed back and forth three times using a 2000 g compression roller at a speed of 300 mm/min. One end of the test sample was bent 180 degrees, the positive electrode material layer of the test sample was manually peeled away from the current collector by 25 mm along a length direction, and then the test sample was fixed on INSTRON 336 tester, so that a peeled surface was aligned with a line of force of the tester (i.e., parallel to a movement direction of the tester when peeling away). The test sample was continuously peeled away with the tester at a speed of 30 mm/min, a peeling force curve was obtained, a mean value in a smooth section (i.e., a section on the peeling force curve which no longer monotonically increases) in a range of 10-50 mm on the curve was taken as a peeling force F0, and then a binding force F between the positive electrode material layer and the current collector in the test sample was equal to F0/the width of the test sample (measurement unit of F is N/m).

Test of Resistance of the Electrode Plate

The to-be-tested electrode plate was placed on a resistance meter testing table and tested under ambient temperature and humidity with a HIOKI BT3563S resistance meter according to the standard GB/T1410-2006. An area of the tested electrode plate sample was 1540.25 mm$^2$, a test voltage was 0.00001 V, a test pressure was greater than or equal to 0.4 ton (T), and a time interval was 10 s.

Test of Cycle Performance of the Battery

At 25° C., the to-be-tested secondary battery was charged to a charging cut-off voltage of 4.30 V at a constant current of 1 C rate, and then charged to a current of 0.05 C or less at a constant voltage, stood for 10 min, then was discharged to a discharging cut-off voltage of 3.3 V at a constant current of 1 C rate, and stood for 10 min, which was a charge and discharge cycle (i.e., one cycle (cls)). According to this method, the battery was subjected to 1000 cycles of charge and discharge cycle test, and a percentage of a discharge capacity of a last cycle in a discharge capacity of a third cycle was a cycle capacity retention rate.

Test of High-Temperature Storage Performance of the Battery

At 25° C., the to-be-tested secondary battery was charged to the charging cut-off voltage of 4.35 V at a constant current of 0.33 C rate, and then charged to a current of 0.05 C or less at a constant voltage, stood for 10 min, then was discharged to the discharging cut-off voltage of 2.8 V at a constant current of 0.33 C rate. The discharge capacity tested was the discharge capacity C0 of the first cycle. The battery was then charged to the charging cut-off voltage of 4.30 V at a constant current of 0.33 C rate, and then charged to a current of 0.05 C or less at a constant voltage. The battery was then stored at 60° C. for 30 days (d), subsequently discharged to the discharging cut-off voltage of 2.8 V at a constant current of 0.33 C rate, stood for 10 min, then was charged to the charging cut-off voltage of 4.35 V at a constant current of 0.33 C rate, and subsequently charged to a current of 0.05 C or less at a constant voltage, stood for 10 min, and then was discharged to the discharging cut-off voltage of 2.8 V at a constant current of 0.33 C rate. The discharge capacity thus tested was a reversible capacity C1 after storage at 60° C. for 15 days, which was a storage cycle. The battery was stored for 180 days (i.e., 12 cycles) according to this method, and a percentage of the reversible capacity C12 after storage at 60° C. for 180 days in a discharge capacity C0 of the first cycle was the high-temperature storage capacity retention rate.

Example 1

(1) Preparation of a Binder Compound:

To a three-neck flask, 6.5 g of a vinylidene fluoride monomer was added, and a chain transfer agent CPP was added, so that a mass ratio of the chain transfer agent to the vinylidene fluoride monomer was 1:4744; the resultant was dissolved in 200 mL of tetrahydrofuran and evacuated, and then N$_2$ was continuously introduced. 0.05 g of an azobisisobutyronitrile initiator was added, the resultant was heated to 70° C. After 12 hours of stirring and reaction at 70° C., the reaction mixture was poured into ice diethyl ether at 0° C. to be settled, and dried, to obtain a solid powder.

The above solid powders were all dissolved in 200 mL of tetrahydrofuran, 0.5 g of LiAlH$_4$ was added, the resultant was stirred and reacted in an ice water bath at 0° C. for 4 hours, and then poured into ice ethyl ether at 0° C. and settled again, to obtain the binder compound.

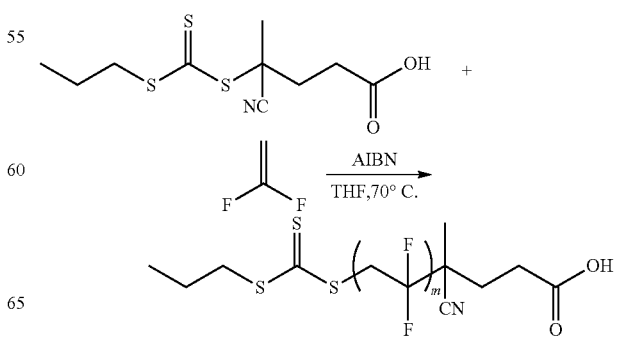

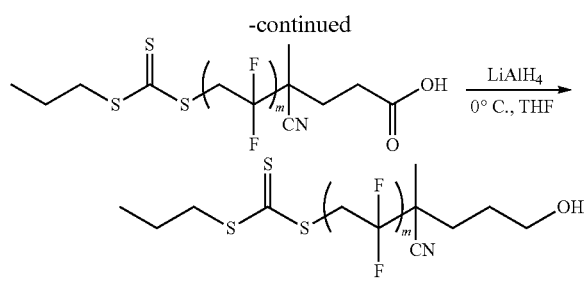

(2) Preparation of a Conductive Binder:

10 g of a conductive agent carbon black SP with a specific surface area of 80 m²/g was weighed and dissolved in 100 ml of tetrahydrofuran, and then 6.4 g of the binder compound obtained in step (1), 0.002 g of 1-(3-dimethylaminopropyl)-3-ethylcarbodiimide hydrochloride (EDC), and 0.002 g of N-hydroxysuccinimide (NHS) as catalysts were well mixed, and the mixture was stirred and reacted at 0° C. for 5 hours and then filtered. An obtained solid was transferred into a beaker, and an appropriate amount of dichloromethane was added for washing. After being stirred for 30 minutes, the resultant was filtered and dried, to obtain the conductive binder powder.

Reaction formula is as follows (dark circles denote the conductive agent carbon black SP particles, same below):

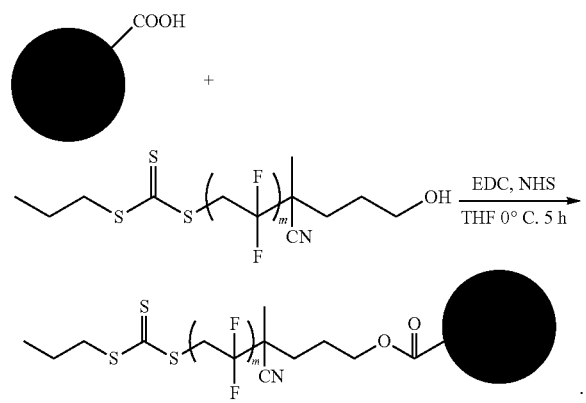

FIG. 1 shows an infrared spectrogram of the conductive binder obtained in this example. In the above, 2883 cm$^{-1}$ is a stretching vibration peak of C—H, 1405 cm$^{-1}$ is CH$_2$ bending vibration, 1186 cm$^{-1}$ and 879 cm$^{-1}$ are C—C skeletal vibration, 615 cm$^{-1}$ and 530 cm$^{-1}$ are CF$_2$ vibration peaks, and 1592 cm$^{-1}$ and 1406 cm$^{-1}$ are symmetric stretching vibration characteristic peak and asymmetric stretching vibration characteristic peak of COO—, respectively, 2883 cm$^{-1}$ is a stretching vibration peak of C—H, 1405 cm$^{-1}$ is CH$_2$ bending vibration, 1186 cm$^{-1}$ and 879 cm$^{-1}$ are C—C skeletal vibration, 615 cm$^{-1}$ and 530 cm$^{-1}$ are CF$_2$ vibration peaks; it can be seen from the infrared spectrum that the binder compound of the present disclosure has been successfully grafted to the SP surface.

(3) Preparation of a Positive Electrode Plate:

After the positive electrode active material lithium iron phosphate (LiFePO$_4$) and the conductive binder prepared in the above step (2) were well mixed at a mass ratio of 96:4, a solvent NMP was added, a solid content was adjusted to be 70 weight % to 80 weight %, and a positive electrode slurry was obtained after well stirring. Then, the positive electrode slurry was coated on a current collector aluminum foil with an electrode plate load of 20 mg/cm², and then the coated current collector aluminum foil is dried, cold-pressed, and cut to obtain the positive electrode plate.

(4) Preparation of a Negative Electrode Plate:

After the graphite, the conductive agent, and sodium carboxymethyl cellulose (CMC-Na) were dry-blended, deionized water was added to adjust the solid content to 45 weight %~55 weight %, and then a binder styrene-butadiene rubber (SBR) was added. The graphite, the conductive agent, the CMC-Na, and the SBR were added at a mass ratio of 96.5:1:1:1.5. After the mixture was stirred well, a negative electrode slurry was obtained, and then coated on a copper foil with an electrode plate load of 11.4 mg/cm². The coated copper foil was dried, cold-pressed, and cut to obtain the negative electrode plate.

(5) Preparation of a Secondary Battery:

The electrode plates prepared in step (3) and step (4) and a separator were wound to form a battery core, and encapsulated with an aluminum plastic film into a dry battery core, followed by processes such as liquid injection (an electrolytic solution is a solution with a concentration of 1 mol/L obtained by dissolving LiPF$_6$ in ethylene carbonate (EC)/dimethyl carbonate (DMC) at a mass ratio of 1:1), formation, and aging, to obtain the secondary battery.

Example 2

(1) Preparation of a Binder Compound:

To a three-neck flask, 6.5 g of a vinylidene fluoride monomer was added, and a chain transfer agent CPP was added, so that a mass ratio of the chain transfer agent to the vinylidene fluoride monomer was 1:4657; the resultant was dissolved in 200 mL of tetrahydrofuran and evacuated, and then N$_2$ was continuously introduced. 0.05 g of an azobisisobutyronitrile initiator was added, the resultant was heated to 70° C. After 12 hours of stirring and reaction at 70° C., the reaction mixture was poured into ice diethyl ether at 0° C. to be settled, and dried, to obtain a solid powder.

The above solid powders were all transferred into a three-necked flask, 200 mL of methanol was added, and ammonia gas was introduced at a reaction temperature of 45° C. After 10 hours of reaction, the resultant was poured into ice ethyl ether at 0° C. to be settled, to obtain a solid.

The above solid was transferred into a round-bottom flask, 2 g of sodium hypochlorite was added, the resultant was dissolved in 200 mL of methanol, then 50 mL of 0.05 mol/L sodium hydroxide was added, the resultant was stirred and reacted at 25° C. for 6 hours, and finally the resulting product was poured into ice ethyl ether at 0° C. to be settled, to obtain the binder compound.

Reaction formulas are as follows:

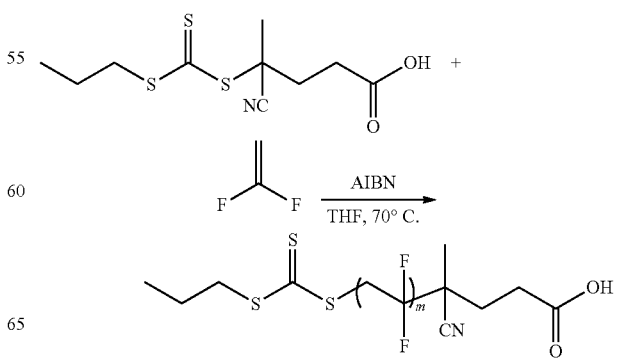

-continued

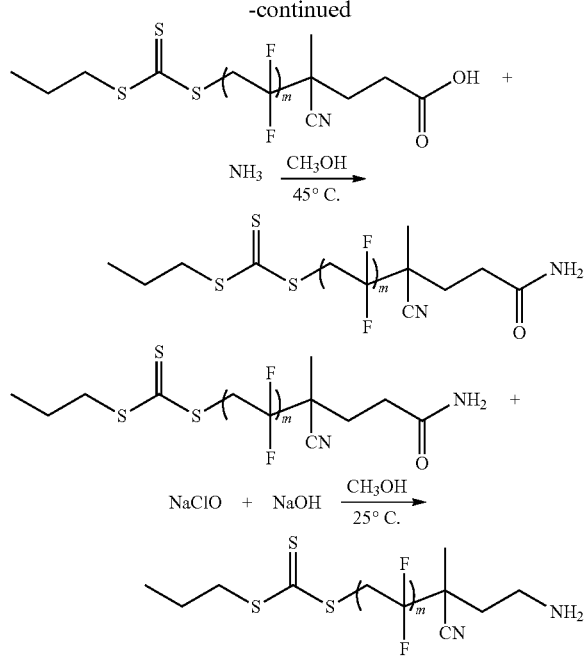

(2) Preparation of a Conductive Binder:

10 g of a conductive agent carbon black SP was dissolved in 100 ml of pyridine, and then 6.4 g of the binder compound prepared in step (1), 0.002 g of $SOCl_2$ (sulfoxide chloride) as catalyst, and 0.1 mg of triethylamine were added and well mixed, and the mixture was stirred and reacted at 0° C. for 3 hours and then filtered. An obtained solid was transferred into a beaker, and an appropriate amount of dichloromethane was added for washing. After being stirred for 30 minutes, the resultant was filtered and dried, to obtain the conductive binder powder of the present disclosure.

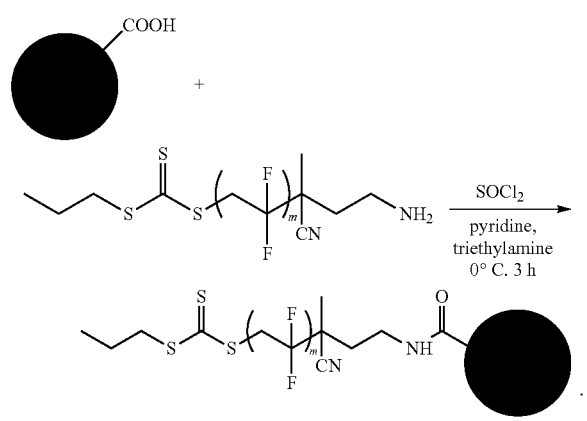

The conductive binder obtained in this example was subjected to infrared spectrum test, wherein 2883 $cm^{-1}$ is a stretching vibration peak of C—H, 1405 $cm^{-1}$ is $CH_2$ bending vibration, 1186 $cm^{-1}$ and 879 $cm^{-1}$ are C—C skeletal vibration, 615 $cm^{-1}$ and 530 $cm^{-1}$ are $CF_2$ vibration peaks, and 3650 $cm^{-1}$ is stretching vibration peak of N—H; and 1680 $cm^{-1}$ is a C—O vibration peak; it can be seen from the infrared spectrum that the binder compound of the present disclosure has been successfully grafted to the SP surface.

The conductive binder was used to prepare the electrode plates and the battery in the same way as in the steps (3)-(5) in Example 1.

Example 3-8

In Examples 3-8, the conditions are the same as those in Example 1 except that the mass ratios of the chain transfer agent to the vinylidene fluoride monomer are different in step 1) and the mass ratios of the binder compound to the conductive carbon black SP are different in step 2).

The amount of the conductive carbon black SP added in the step 2) is shown in Table 1.

TABLE 1

| Mass ratios of the binder compound to the conductive carbon black SP in Examples 1-8 | | | | | | | |
|---|---|---|---|---|---|---|---|
| Examples | 1 | 3 | 4 | 5 | 6 | 7 | 8 |
| Addition amount of SP (g) | 10 | 64 | 40 | 21.3 | 6.4 | 2 | 1.3 |
| Mass ratio of binder compound to SP | 0.64:1 | 0.1:1 | 0.16:1 | 0.3:1 | 1:1 | 3.1:1 | 4.9:1 |

See Table 5 below for test values of the performances of the binder compounds, the electrode plates, and the batteries obtained in various above examples.

Example 9-14

In Examples 9-14, the conditions are the same as those in Example 1 except that the mass ratios of the chain transfer agent to the vinylidene fluoride monomer are different in step 1) and the specific surface areas of the conductive carbon blacks SP are different in step 2).

The specific surface areas of the conductive carbon black SP in step 2) in various examples are shown in Table 2.

TABLE 2

| Specific surface areas of the conductive carbon black SP | | | | | | | |
|---|---|---|---|---|---|---|---|
| Examples | 1 | 9 | 10 | 11 | 12 | 13 | 14 |
| Specific surface area of SP ($m^2/g$) | 80 | 10 | 30 | 350 | 550 | 750 | 1000 |

See Table 5 below for test values of the performances of the binder compounds, the electrode plates, and the batteries obtained in various above examples.

Example 15-20

In Examples 15-20, the conditions are the same as those in Example 1 except that the mass ratios of the chain transfer agent to the vinylidene fluoride monomer are different in step 1) and the amounts of the conductive binder added are different in step 3).

In the preparation of the electrode plates in various examples, the weight percentages of the conductive binder contained in the positive electrode material layer are shown in Table 3.

TABLE 3

Weight percentages of the conductive binder contained in the positive electrode material layer (weight %)

| Examples | 1 | 15 | 16 | 17 | 18 | 19 | 20 |
|---|---|---|---|---|---|---|---|
| weight % | 4 | 0.5 | 1 | 3 | 6 | 10 | 12 |

See Table 5 below for test values of the performances of the electrode plates and the batteries obtained in various above examples.

Figure 2:
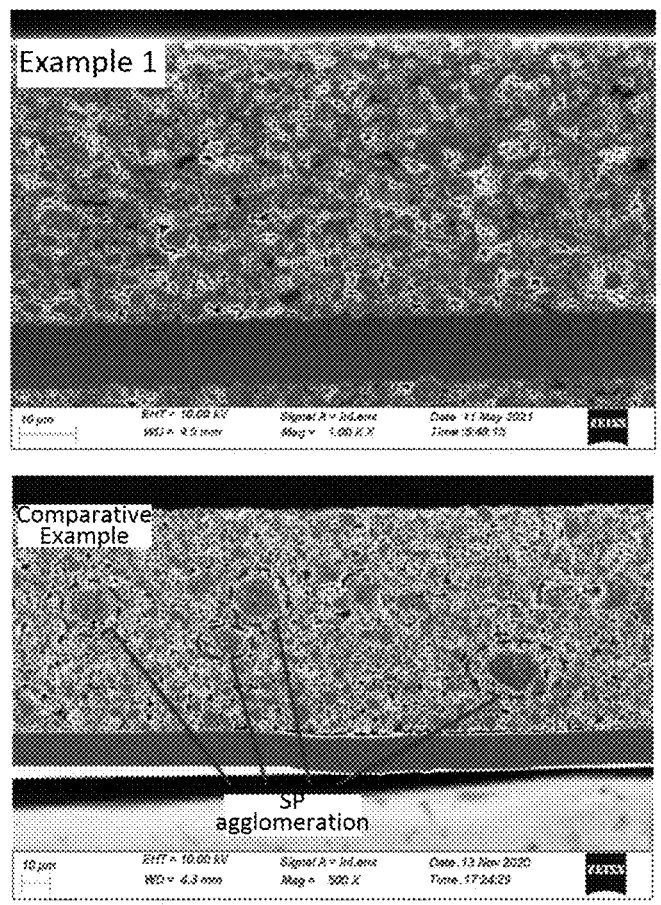
FIG. 2 is scanning electron micrographs showing section morphologies of positive electrode plates of Example 1 and Comparative Example C1.

See Table 5 below for relevant performance test data. FIG. 2 shows scanning electron micrographs of section morphologies of the positive electrode plates of Example 1 and Comparative Example C1 of the present disclosure. It can be seen from the drawing that, in the positive electrode plate of Comparative Example C1, under a magnification of 500 times, it can be seen that the conductive agent obviously agglomerates and is unevenly distributed; and in the positive electrode plate of Example 1, under a magnification of 1000 times, the conductive agent hardly agglomerates and is significantly distributed more uniformly.

The electrode plates and the batteries prepared in various examples and comparative examples in the above were tested. Table 5 shows the test results of the performances of the electrode plates and the batteries prepared in the above Examples 1-20 and Comparative Example C1:

TABLE 5

Molecular weight Mn and number m of units of the binder compound and performance data of the electrode plate and the battery

| Examples | Mass ratio of chain transfer agent to vinylidene fluoride monomer | Number average molecular weight (Mn) | Number of unit (m) | Binding force of electrode plate (N/m) | Resistance of electrode plate (ohm) | Storage capacity retention rate (180 d@60° C.) | Cycle capacity retention rate (1000 cls @25° C.) |
|---|---|---|---|---|---|---|---|
| 1 | 1:4744 | 1310000 | 20154 | 16.3 | 0.565 | 91.1% | 87.9% |
| 2 | 1:4657 | 1290000 | 19846 | 16.5 | 0.570 | 91.0% | 87.7% |
| 3 | 1:4693 | 1300000 | 20000 | 18.3 | 0.662 | 89.3% | 87.9% |
| 4 | 1:4675 | 1295000 | 19923 | 10.2 | 0.676 | 91.4% | 85.8% |
| 5 | 1:4675 | 1295000 | 19923 | 20.6 | 0.571 | 93.6% | 88.7% |
| 6 | 1:4657 | 1290000 | 19846 | 20.1 | 0.362 | 94.3% | 89.8% |
| 7 | 1:4693 | 1300000 | 20000 | 20.9 | 0.390 | 90.5% | 87.2% |
| 8 | 1:4693 | 1300000 | 20000 | 22.3 | 0.398 | 90.1% | 87.1% |
| 9 | 1:4729 | 1310000 | 20153 | 10.2 | 0.873 | 90.4% | 84.8% |
| 10 | 1:4657 | 1290000 | 19846 | 11.3 | 0.781 | 90.5% | 85.1% |
| 11 | 1:4693 | 1300000 | 20000 | 17.5 | 0.527 | 91.3% | 88.5% |
| 12 | 1:4693 | 1300000 | 20000 | 18.8 | 0.405 | 91.8% | 90.1% |
| 13 | 1:4693 | 1300000 | 20000 | 20.3 | 0.375 | 92.4% | 90.8% |
| 14 | 1:4657 | 1290000 | 19846 | 21.6 | 0.256 | 89.5% | 88.3% |
| 15 | 1:4675 | 1295000 | 19923 | 8.5 | 0.890 | 88.3% | 84.6% |
| 16 | 1:4657 | 1290000 | 19846 | 10.8 | 0.670 | 89.5% | 86.3% |
| 17 | 1:4729 | 1310000 | 20153 | 17.8 | 0.540 | 90.7% | 87.3% |
| 18 | 1:4693 | 1300000 | 20000 | 20.4 | 0.300 | 95.5% | 91.1% |
| 19 | 1:4729 | 1310000 | 20153 | 21.4 | 0.270 | 95.3% | 91.7% |
| 20 | 1:4657 | 1290000 | 19846 | 21.9 | 0.250 | 94.8% | 90.5% |
| C1 | | 1300000 | 20000 | 20.7 | 0.832 | 90.2% | 85.4% |

Comparative Example C1

Preparation of the Positive Electrode Plate:

A positive electrode active material (lithium iron phosphate (LiFePO$_4$)), a conductive carbon black SP with a specific surface area of 580 m$^2$/g, and a binder polyvinylidene fluoride (PVDF) were added at a mass ratio of 96:2.5:1.5 and well mixed, then a solvent NMP was added, to adjust the solid content to 70 weight %-80 weight %. After the resultant was well stirred, a positive electrode slurry was obtained, then the positive electrode slurry was coated on an aluminum foil also with a positive electrode plate load of 20 mg/cm$^2$, and then the coated aluminum foil was dried, cold-pressed, and cut to obtain the positive electrode plate; and then, the secondary battery was prepared in the same way as in steps (4)-(5) in Example 1.

It can be seen from Examples 1 and 3-8 that when the mass ratio of the binder moiety to the carbon-based conductive agent moiety in the conductive binder is 0.1-5:1, the conductive binder has good binding performance and conductive performance, and the storage and cycle performances of the secondary battery prepared thereby are improved compared with Comparative Example C1. In particular, within the range of 0.3-1:1, the binding performance and the conductive performance of the conductive binder, and the storage and cycle performances of the battery are all obviously improved.

It can be seen from Examples 1 and 9-14 that, when the carbon black used has a specific surface area in the range of 1-3000 m$^2$/g, optionally in the range of 10-1200 m$^2$/g, and more particularly in the range of 20-800 m$^2$/g, the conductive binder has a good binding property and electric conductivity, and the storage and cycle performances of the battery are also obviously improved compared with that in Comparative Example C1.

It can be seen from Examples 1 and 16-20 that when the conductive binder contained in the positive electrode material layer is within the range of 1-10 weight %, particularly in the range of 3-6 weight %, both the cycle and storage performances of the battery are obviously improved compared with Comparative Example C1.

As the proportion of the conductive binder in the positive electrode material layer is increased, the proportion of the active material therein is correspondingly decreased, which leads to decrease in the battery capacity. In Example 1, the conductive binder content is 4 weight %, and the battery capacity is tested to be 2.5 Ah; while when the content of the conductive binder is increased to 12 weight %, the battery capacity of Example 20 drops to 2.0 Ah. Those skilled in the art could know that if the content of the conductive binder continues to increase, the content of the active material continues to decrease correspondingly, and the battery capacity will continue to drop. Therefore, by controlling the content of the conductive binder in the positive electrode material layer to be 1-10 weight %, the battery with better comprehensive performances can be obtained.

In conclusion, compared with Comparative Example C1, the conductive binder, the electrode plate, and the battery of the present disclosure can make the secondary battery obtain balanced and improved storage and cycle performances.

It should be noted that the present disclosure is not limited to the above embodiments. The above embodiments are merely examples, and embodiments having substantially the same configuration and exerting the same effects as the technical idea within the scope of the technical solutions of the present disclosure are all included in the technical scope of the present disclosure. In addition, in the scope without departing from the gist of the present disclosure, various modifications that could be conceived by those skilled in the art and applied to the embodiments, and other modes constructed by combining a part of the constituent elements of the embodiments are also included in the scope of the present disclosure.

What is claimed is:

1. A binder compound, which has a structure of formula (I):

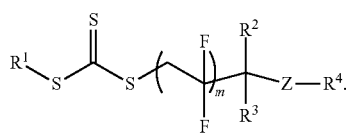

wherein $R^1$ and $R^2$ each independently represent a straight or branched $C_{1-12}$ alkyl; $R^3$ represents a halogen or cyano group; $R^4$ represents a hydroxymethyl or amino; Z represents a straight or branched $C_{1-12}$ alkylene; and m represents an integer selected from 7600-47000.

2. The binder compound according to claim 1, wherein $R^1$ and $R^2$ each independently represents a straight or branched $C_{2-8}$ alkyl; $R^3$ represents a cyano group; and Z represents a straight or branched $C_{2-8}$ alkylene.

3. The binder compound according to claim 1, which has a following structure:

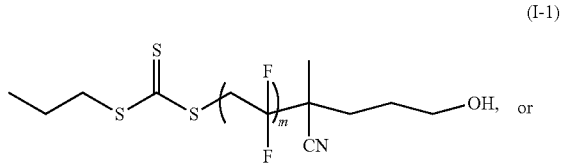

wherein m represents an integer selected from 7600-47000.

4. A preparation method of a binder compound, the method comprising:
(i) making, in presence of an initiator, a chain transfer agent of formula (II) to undergo a polymerization reaction with a vinylidene fluoride monomer in a solvent:

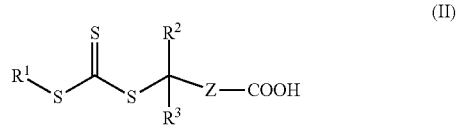

wherein $R^1$ and $R^2$ each independently represents a straight or branched $C_{1-12}$ alkyl, $R^3$ represents a halogen or cyano group, and Z represents a straight or branched $C_{1-12}$ alkylene;
(ii) making a reaction product obtained in step (i) to react with a reducing agent in a solvent to obtain a compound of a following formula (I); or
(iii) making the reaction product obtained in step (i) react with an amination agent in a solvent; and
(iv) making a reaction product obtained in step (iii) to react with an oxidant under an alkaline condition, to obtain a binder compound of the following formula (I),

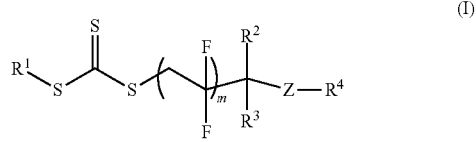

wherein $R^4$ represents a hydroxymethyl or amino; and m represents an integer selected from 7600-47000.

5. The method according to claim 4, wherein the step (i) is carried out at 60-80° C.

6. The method according to claim 4, wherein a mass ratio of the chain transfer agent to the vinylidene fluoride monomer in the step (i) is 1:1783 to 1:11029.

7. The method according to claim 4, wherein the chain transfer agent in the step (i) is 4-cyano-4-(((propylthio)carbonothioyl)thio)pentanoic acid of formula (II-1):

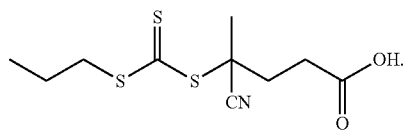

(II-1)

8. The method according to claim 4, wherein the step (ii) is carried out at −10-10° C.

9. The method according to claim 4, wherein the step (iii) is carried out at 35-60° C.

10. The method according to claim 4, wherein the step (iv) is carried out at 15-50° C.

11. A conductive binder, which contains a carbon-based conductive agent moiety and a binder moiety covalently linked to the carbon-based conductive agent moiety, wherein the binder moiety has a structure of formula (III):

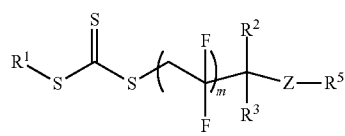

(III)

wherein $R^1$ and $R^2$ each independently represents a straight or branched $C_{1-12}$ alkyl, $R^3$ represents a halogen or cyano group, $R^4$ represents a hydroxymethyl or amino; Z represents a straight or branched $C_{1-12}$ alkylene; and m represents an integer selected from 7600-47000; $R^5$ represents #-CH$_2$OC(O)-* or #-NHC(O)-*, and # represents a position linked to Z, and * indicates a position covalently linked to the carbon-based conductive agent moiety.

12. The conductive binder according to claim 11, wherein the binder moiety has a following structure:

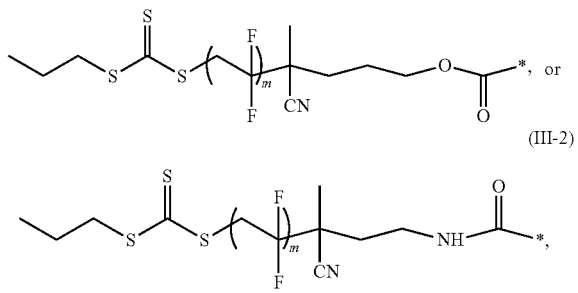

(III-1)

(III-2)

where * indicates a position covalently linked to the carbon-based conductive agent moiety, and m represents an integer selected from 7600-47000.

13. The conductive binder according to claim 11, wherein a mass ratio of the binder moiety to the carbon-based conductive agent moiety is 0.1-5:1.

14. The conductive binder according to claim 11, wherein a specific surface area of the carbon-based conductive agent moiety is 1-3000 m²/g.

15. The conductive binder according to claim 11, wherein the carbon-based conductive agent moiety is one or more selected from the group consisting of superconducting carbon, carbon black SP, acetylene black, ketjen black, carbon dots, carbon nanotube, graphene, carbon nanofiber.

16. A preparation method of a conductive binder, the method comprising:
making a binder compound of formula (I), a carbon-based conductive agent, and a catalyst to react in a solvent to obtain a conductive binder:

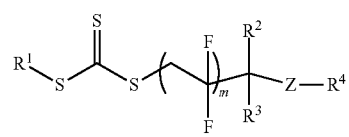

(I)

where $R^1$ and $R^2$ each independently represents a straight or branched $C_{1-12}$ alkyl, $R^3$ represents a halogen or cyano group, $R^4$ represents a hydroxymethyl or amino; Z represents a straight or branched $C_{1-12}$ alkylene; and m represents an integer selected from 7600-47000.

17. The method according to claim 16, wherein $R^1$ and $R^2$ each independently represents a straight or branched $C_{2-8}$ alkyl; $R^3$ represents a cyano group; and Z represents a straight or branched $C_{2-8}$ alkylene.

18. The method according to claim 16, wherein the binder compound of the formula (I) has a following structure:

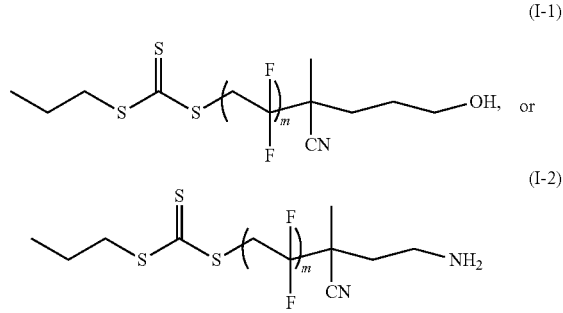

(I-1)

(I-2)

wherein m represents an integer selected from 7600-47000.

19. The method according to claim 16, wherein the reaction is carried out at −5-5° C.

20. The method according to claim 16, wherein a mass ratio of the binder compound to the carbon-based conductive agent is 0.1-5:1.

* * * * *